US009320899B2

(12) United States Patent
Parramon et al.

(10) Patent No.: US 9,320,899 B2
(45) Date of Patent: Apr. 26, 2016

(54) LOW POWER LOSS CURRENT DIGITAL-TO-ANALOG CONVERTER USED IN AN IMPLANTABLE PULSE GENERATOR

(71) Applicant: Boston Scientific Neuromodulation Corporation, Valencia, CA (US)

(72) Inventors: Jordi Parramon, Valencia, CA (US); Yuping He, Northridge, CA (US); Kiran Nimmagadda, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/292,176

(22) Filed: May 30, 2014

(65) Prior Publication Data
US 2014/0277270 A1 Sep. 18, 2014

Related U.S. Application Data

(63) Continuation of application No. 12/424,916, filed on Apr. 16, 2009, now Pat. No. 8,750,985, which is a continuation of application No. 11/138,632, filed on May 26, 2005, now Pat. No. 7,539,538.

(60) Provisional application No. 60/575,725, filed on May 28, 2004.

(51) Int. Cl.
*A61N 1/36* (2006.01)
*A61N 1/02* (2006.01)
*A61N 1/378* (2006.01)

(52) U.S. Cl.
CPC ............ *A61N 1/36071* (2013.01); *A61N 1/025* (2013.01); *A61N 1/36125* (2013.01); *A61N 1/378* (2013.01)

(58) Field of Classification Search
None
See application file for complete search history.

(56) References Cited

U.S. PATENT DOCUMENTS

| 3,646,940 | A | | 3/1972 | Timm et al. |
|---|---|---|---|---|
| 3,724,467 | A | | 4/1973 | Avery et al. |
| 3,822,708 | A | | 7/1974 | Zilber |
| 4,285,345 | A | | 8/1981 | Mensink et al. |
| 4,686,991 | A | | 8/1987 | Dufresne et al. |
| 4,947,844 | A | | 8/1990 | McDermott |
| 4,949,720 | A | | 8/1990 | Thompson |
| 5,025,204 | A | | 6/1991 | Su |
| 5,836,983 | A | | 11/1998 | Weijand et al. |
| 5,941,906 | A | * | 8/1999 | Barreras, Sr. ...... A61N 1/36071 607/60 |
| 6,181,969 | B1 | | 1/2001 | Gord |
| 6,516,227 | B1 | | 2/2003 | Meadows et al. |

(Continued)

*Primary Examiner* — Erica Lee
(74) *Attorney, Agent, or Firm* — Lewis, Reese & Nesmith, PLLC

(57) ABSTRACT

An implantable stimulation device that includes output current sources and/or sinks configured to provide an output current for a load (i.e., tissue). The output path of the output current source or sink comprises a transistor which operates in a linear mode instead of a saturation mode. Because operation in a linear mode results in smaller drain-to-source voltage drops, power consumption in the output current source or sink (and hence in the implantable stimulator) is reduced, reducing battery or other power source requirements. Operation in the linear mode is facilitated by a load in an input path and a load in the output path (which bears the output current). The loads can be active transistors or passive resistors. A feedback circuit (e.g., an operational amplifier) receives voltages that build up across these loads, and sends a control signal to the gate of the transistor to ensure its linear operation.

26 Claims, 9 Drawing Sheets

(56) References Cited

U.S. PATENT DOCUMENTS 6,558,377 B2 5/2003 Lee et al.
7,180,760 B2 2/2007 Varrichio et al.
7,539,538 B2 5/2009 Parramon et al.
7,805,189 B2 9/2010 Stein et al.

\* cited by examiner

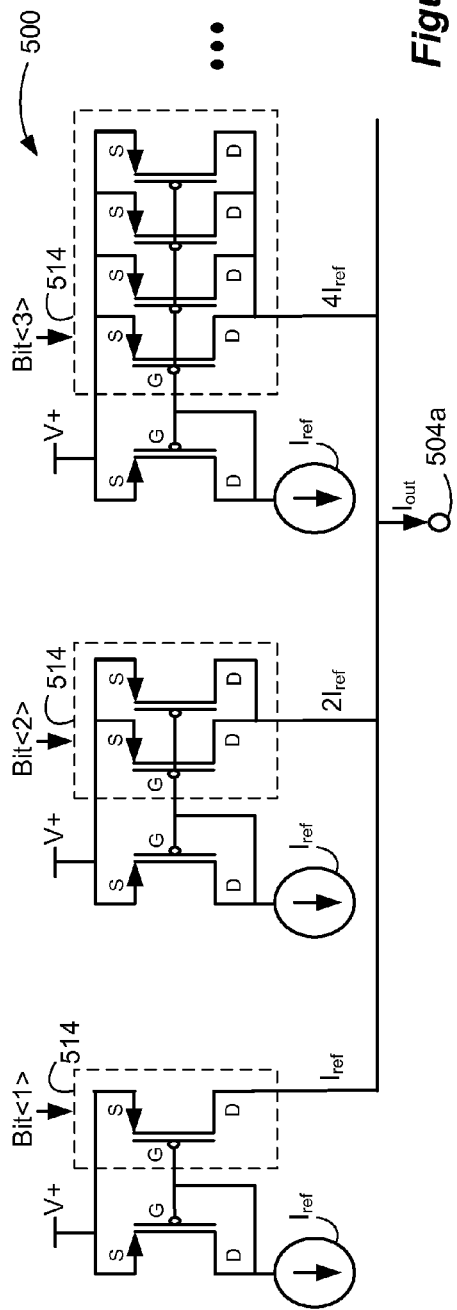
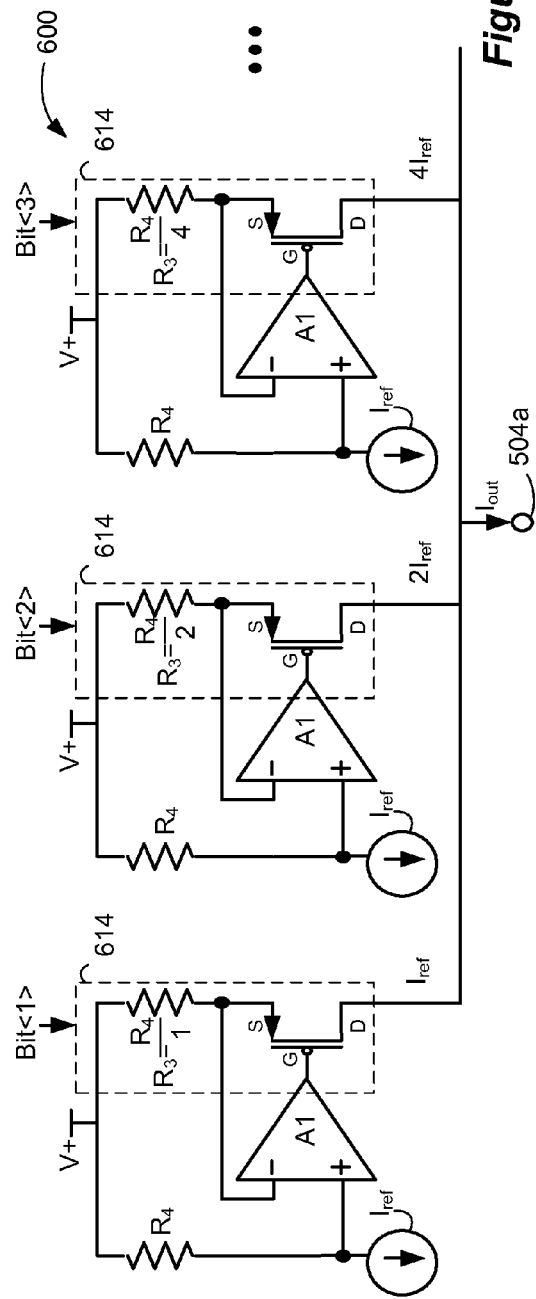
*Figure 7A*
*Figure 7B*

LOW POWER LOSS CURRENT DIGITAL-TO-ANALOG CONVERTER USED IN AN IMPLANTABLE PULSE GENERATOR

CROSS-REFERENCE TO RELATED APPLICATIONS

This application is a continuation of U.S. patent application Ser. No. 12/424,916, filed Apr. 16, 2009, which is a continuation of U.S. patent application Ser. No. 11/138,632, filed May 26, 2005 (now U.S. Pat. No. 7,539,538), which is a non-provisional application of U.S. Provisional Patent Application Ser. No. 60/575,725, filed May 28, 2004. Priority is claimed to these previous applications, and they are incorporated herein by reference in their entireties.

FIELD OF THE INVENTION

The present invention relates generally to implantable pulse generators, e.g., a pulse generator used within a Spinal Cord Stimulation (SCS) system or other type of neural stimulation system. More particularly, the present invention relates to the use of output current sources having a current digital to analog converter (DAC) configured to regulate the current delivered via an implantable pulse generator (IPG).

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The present invention may find applicability in all such applications, although the description that follows will generally focus on the use of the invention within a spinal cord stimulation system, such as that disclosed in U.S. Pat. No. 6,516,227, issued Feb. 4, 2003 in the name of inventors Paul Meadows et al., which is incorporated herein by reference in its entirety.

Spinal cord stimulation is a well accepted clinical method for reducing pain in certain populations of patients. A Spinal Cord Stimulation (SCS) system typically includes an Implantable Pulse Generator (IPG) or Radio-Frequency (RF) transmitter and receiver, electrodes, at least one electrode lead, and, optionally, at least one electrode lead extension. The electrodes, which reside on a distal end of the electrode lead, are typically implanted along the dura of the spinal cord, and the IPG or RF transmitter generates electrical pulses that are delivered through the electrodes to the nerve fibers within the spinal column. Individual electrode contacts (the "electrodes") are arranged in a desired pattern and spacing to create an electrode array. Individual wires within one or more electrode leads connect with each electrode in the array. The electrode lead(s) exit the spinal column and generally attach to one or more electrode lead extensions. The electrode lead extensions, in turn, are typically tunneled around the torso of the patient to a subcutaneous pocket where the IPG or RF receiver is implanted. Alternatively, the electrode lead may directly connect with the IPG or RF receiver.

SCS and other stimulation systems are known in the art. For example, an implantable electronic stimulator is disclosed in U.S. Pat. No. 3,646,940, issued Mar. 7, 1972, entitled "Implantable Electronic Stimulator Electrode and Method," which teaches timed sequenced electrical pulses to a plurality of electrodes. Another example, U.S. Pat. No. 3,724,467, issued Apr. 3, 1973, entitled "Electrode Implant for the Neuro-Stimulation of the Spinal Cord," teaches an electrode implant for neuro-stimulation of the spinal cord. A relatively thin and flexible strip of biocompatible material is provided as a carrier on which a plurality of electrodes reside. The electrodes are connected by a conductor, e.g., a lead body, to an RF receiver, which is also implanted and is controlled by an external controller.

U.S. Pat. No. 3,822,708, issued Sep. 9, 1974, entitled "Electrical Spinal Cord Stimulating Device and Method for Management of Pain," teaches an SCS device with five aligned electrodes which are positioned longitudinally along the spinal cord. Current pulses applied to the electrodes block sensed intractable pain, while allowing passage of other sensations. The stimulation pulses applied to the electrodes have a repetition rate of 5 to 200 pulses per second. A patient-operated switch allows the patient to change the electrodes that are activated (i.e., which electrodes receive the stimulation pulses) to stimulate a specific area of the spinal cord, as required, to better block the pain.

Regardless of the application, all implantable pulse generators are active devices requiring energy for operation. The energy is supplied by a power source that may be an implanted battery or an external power source. It is desirable for the implantable pulse generator to operate for extended periods of time with little intervention by the patient or caregiver. However, devices powered by primary (non-rechargeable) batteries have a finite lifetime before the device must be surgically removed and replaced. Frequent surgical replacement is not an acceptable alternative for many patients. If a battery is used as the energy source, it must have a large enough storage capacity to operate the device for a reasonable length of time. For low-power devices (less than 100 µW) such as cardiac pacemakers, a primary battery may operate for a reasonable length of time, often up to ten years. However, in many neural stimulation applications such as SCS, the power requirements are considerably greater due to higher stimulation rates, pulse widths, or stimulation thresholds.

Thus, one challenge with IPGs is keeping power usage to a minimum to conserve battery life. While increasing battery life may be achieved by extending the size of the battery, that runs counter to the goal of reducing the overall device size which is determined partly by battery size. Conservation of energy in an implantable, battery operated device is an important design goal to reduce the overall size of the device and to prolong the life of the battery, thus deferring surgery to replace the device.

An IPG often includes one or more output current sources that are configured to supply current to a load, such as tissue, associated with the IPG. The output current source may include a current digital to analog converter (DAC) configured to regulate the current that is delivered to the load. However, the DAC is often physically located in series with the load. Hence, any load current passes through the DAC as well, which results in a power loss. This power loss may result in a shortening of the battery life of the IPG. The power loss is directly proportional to the voltage drop across the DAC. Accordingly, there is a great need for an IPG having an output current source that includes a current DAC having a small voltage drop such that the power efficiency of the IPG is maximized.

SUMMARY

In one embodiment, the present invention provides an implantable stimulation device that includes output current sources and/or sinks configured to provide an output current for a load. The output path of the output current source or sink comprises a transistor which operates in a linear mode instead of a saturation mode. Because operation in a linear mode results in smaller drain-to-source voltage drops, power consumption in the output current source or sink (and hence in the implantable stimulator) is reduced, reducing battery or other power source requirements. Operation in the linear mode is facilitated in useful embodiments by a load in an input path (into which a reference current is sent) and a load in the output path (which bears the output current). The loads can be active transistors or passive resistors. A feedback circuit (e.g., an operational amplifier) receives voltages that build up across these loads, and sends a control signal to the gate of the transistor to ensure its linear operation.

In preferred embodiments, the output current sources or sinks comprise a digital-to-analog converter (DAC) for scaling the magnitude of the output current versus the input reference current. Moreover, in other embodiments, the values of the loads are varied (by a ratio of N) to allow the output current to be amplified with respect to the reference current, without the necessity of adding further output stages in parallel.

BRIEF DESCRIPTION OF THE DRAWINGS

The above and other aspects of the present invention will be more apparent from the following more particular description thereof, presented in conjunction with the following drawings wherein:

FIGS. 7A and 7B show how use of the design of the output current source or sink of FIG. 6 (FIG. 7B) minimizes layout complexity as compared to the output current source or sink of FIG. 5 (FIG. 7A);

Corresponding reference characters indicate corresponding components throughout the several views of the drawings.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims.

At the outset, it is noted that the present invention may be used with an implantable pulse generator (IPG), or similar electrical stimulator and/or electrical sensor, that may be used as a component of numerous different types of stimulation systems. The description that follows relates to use of the invention within a spinal cord stimulation (SCS) system. However, it is to be understood that the invention is not so limited. Rather, the invention may be used with any type of implantable electrical circuitry that could benefit from an output current source having a current DAC topology configured to maximize energy efficiency. For example, the present invention may be used as part of a pacemaker, a defibrillator, a cochlear stimulator, a retinal stimulator, a stimulator configured to produce coordinated limb movement, a cortical and deep brain stimulator, or in any other neural stimulator configured to treat urinary incontinence, sleep apnea, shoulder sublaxation, etc.

Figure 1:
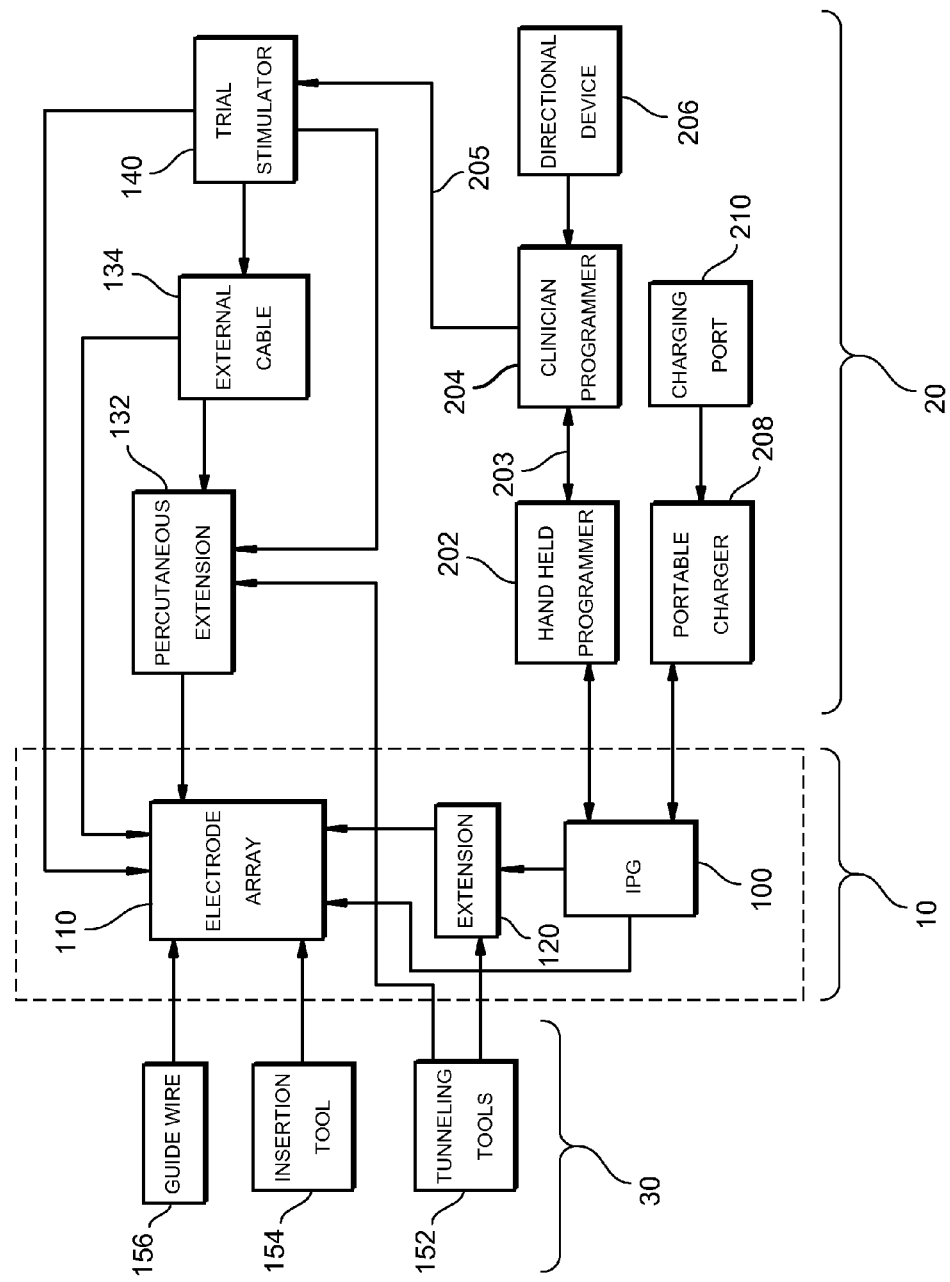
FIG. 1 shows a block diagram that illustrates the various implantable, external, and surgical components of a spinal cord stimulation (SCS) system that employs an implantable pulse generator (IPG) having a rechargeable battery in accordance with the present invention.

Turning first to FIG. 1, a block diagram is shown that illustrates the various components of an exemplary SCS system in which the invention may be used. These components may be subdivided into three broad categories: (1) implantable components 10, (2) external components 20, and (3) surgical components 30. As seen in FIG. 1, the implantable components 10 include an implantable pulse generator (IPG) 100, an electrode array 110, and (as needed) a lead extension 120. The extension 120 may be used to electrically connect the electrode array 110 to the IPG 100. In an exemplary embodiment, the IPG 100, described more fully below in connection with FIG. 3 or 4, may comprise a rechargeable, multichannel, sixteen contact, telemetry-controlled, pulse generator housed in a rounded high-resistivity titanium alloy case to reduce eddy current heating during the inductive charging process. The embodiment may include sixteen current sources, each with a programmable amplitude such that the device is a current-regulated, rather than a voltage-regulated system. However, it will be noted that in an alternative embodiment, a SCS system may include more or less than sixteen current sources.

According to an exemplary embodiment of the present invention, the IPG 100 may include stimulating electrical circuitry ("stimulating electronics"), a power source, e.g., a rechargeable battery, and a telemetry system. Typically, the IPG 100 is placed in a surgically-made pocket either in the abdomen, or just at the top of the buttocks. It may, of course, also be implanted in other locations of the patient's body. Once implanted, the IPG 100 is connected to the lead system, comprising the lead extension 120, if needed, and the electrode array 110. The lead extension 120, for example, may be tunneled up to the spinal column. Once implanted and any trial stimulation period is complete, the lead system 110 and lead extension 120 are intended to be permanent. In contrast, the IPG 100 may be replaced when its power source fails or is no longer rechargeable.

Advantageously, the IPG 100 may provide electrical stimulation through a multiplicity of electrodes, e.g., sixteen electrodes, included within the electrode array 110.

Figure 2:
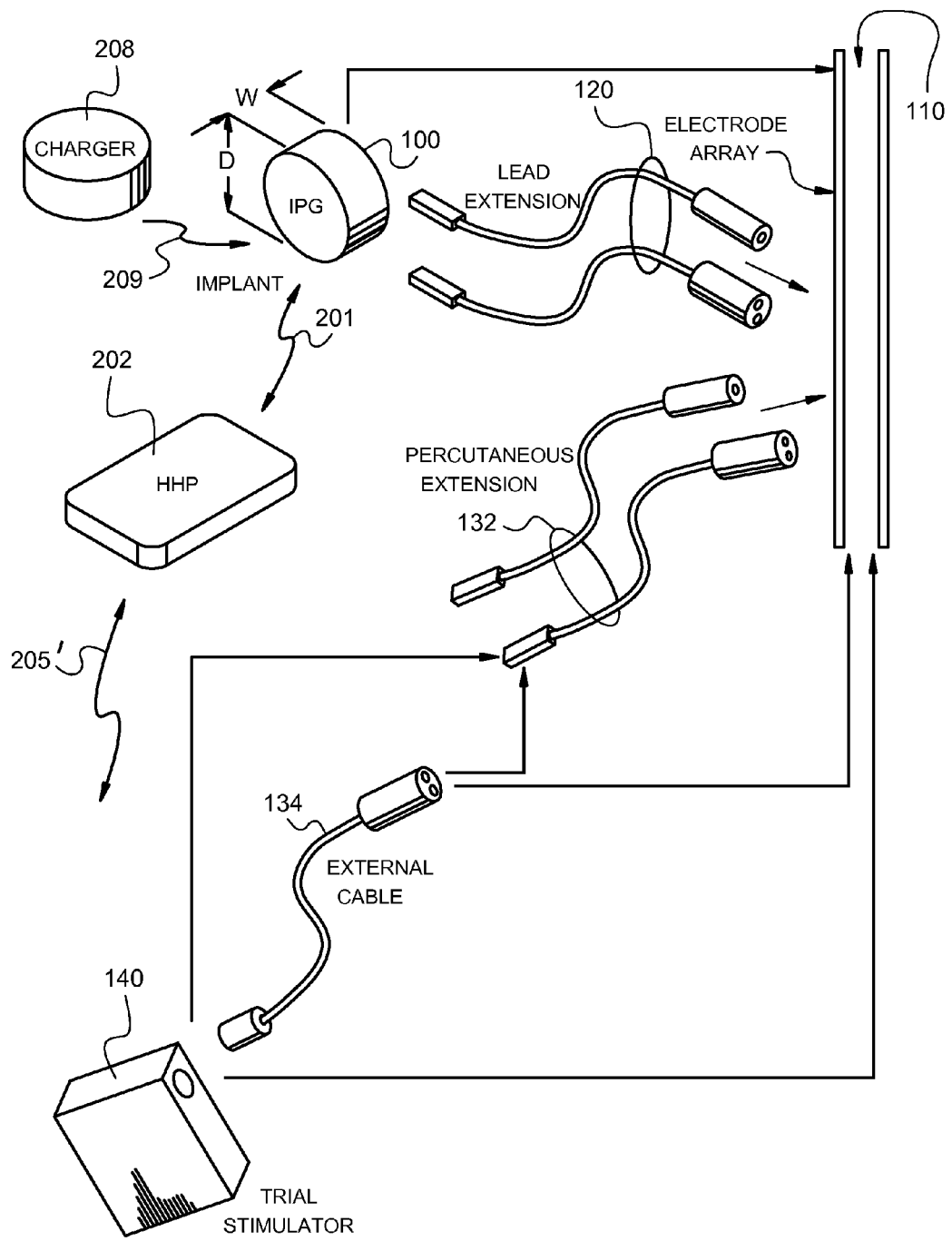
FIG. 2 shows various components of the SCS system of FIG. 1.

As seen best in FIG. 2, and as also illustrated in FIG. 1, the electrode array 110 and its associated lead system typically interface with the implantable pulse generator (IPG) 100 via a lead extension system 120. The electrode array 110 may also be connected to an external trial stimulator 140, through the use of a percutaneous lead extension 132 and/or an external cable 134. The external trial stimulator 140 includes the same pulse generation circuitry as does the IPG 100, and is used on a trial basis for, e.g., 7-10 days after the electrode array has been implanted, prior to implantation of the IPG 100, to test the effectiveness of the stimulation that is to be provided.

Still with reference to FIGS. 1 and 2, the hand-held programmer (HHP) 202 may be used to control the IPG 100 via a suitable non-invasive communications link 201, e.g., an RF link. Such control allows the IPG 100 to be turned ON or OFF, and generally allows stimulation parameters, e.g., pulse amplitude, width, and rate, to be set within prescribed limits. The HHP 202 may also be linked with the external trial stimulator 140 through another link 205', e.g., an infra red link. Detailed programming of the IPG 100 is preferably accomplished through the use of an external clinician's programmer 204 (FIG. 1), which may also be hand-held and which may be coupled to the IPG 100 directly or through the HHP 202. An external charger 208, non-invasively coupled with the IPG 100 through link 209, e.g., an inductive link, allows energy stored or otherwise made available to the charger 208 to be coupled into the rechargeable battery housed within the IPG 100.

Figure 3:
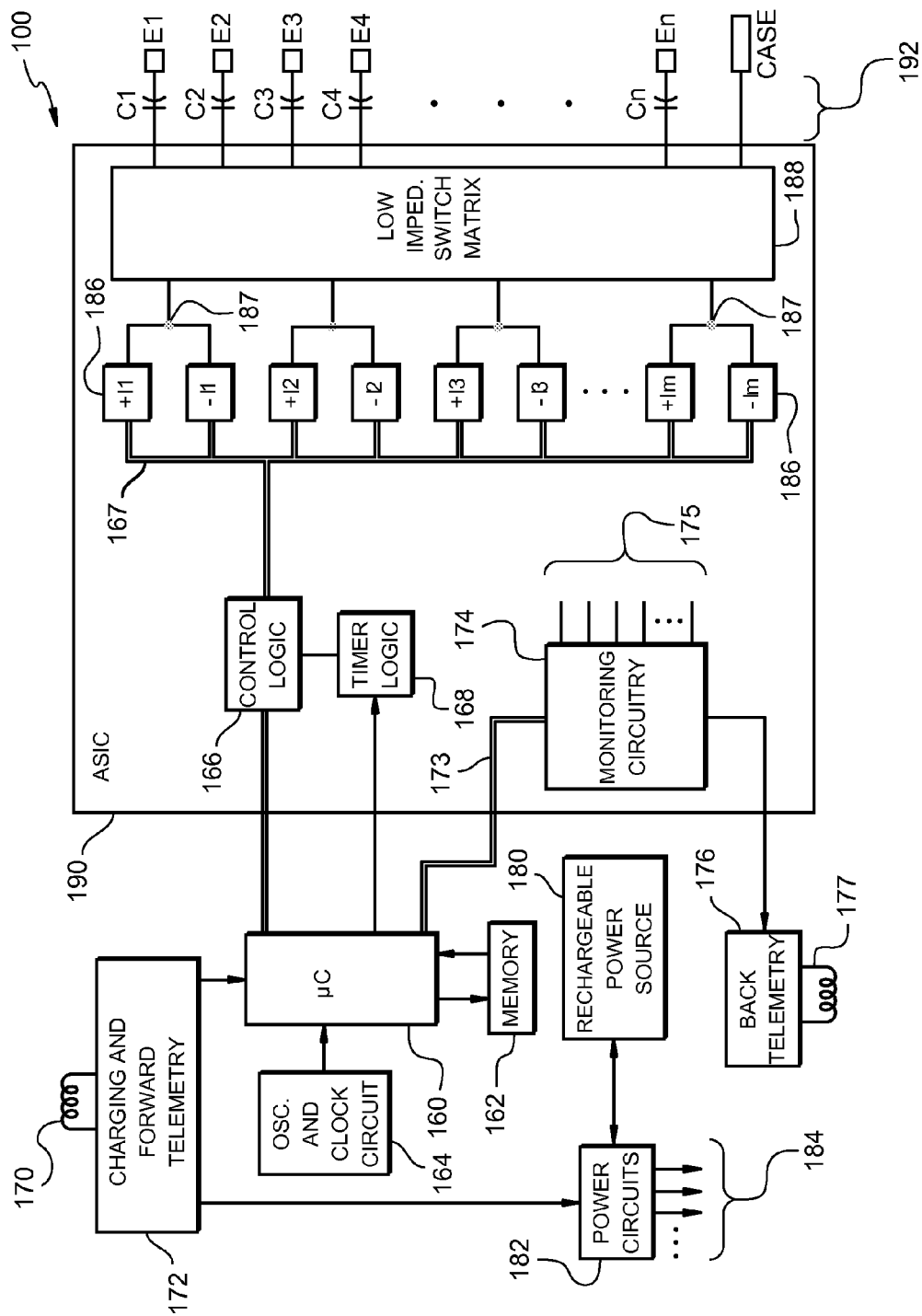
FIG. 3 shows a block diagram that illustrates the main components, including a rechargeable battery, of one embodiment of an implantable pulse generator (IPG) used with the invention.

Turning next to FIG. 3, a block diagram is shown that illustrates the main components of one embodiment of an implantable pulse generator (IPG) 100 that may be used with the invention. As seen in FIG. 3, the IPG may include a microcontroller (μC) 160 connected to memory circuitry 162. The μC 160 typically comprises a microprocessor and associated logic circuitry, which in combination with control logic circuits 166, timer logic 168, and an oscillator and clock circuit 164, generate the necessary control and status signals which allow the μC 160 to control the operation of the IPG in accordance with a selected operating program and stimulation parameters. The operating program and stimulation parameters are typically stored within the memory 162 by transmitting an appropriate modulated carrier signal through a receiving coil 170 and charging and forward telemetry circuitry 172 from an external programming unit, e.g., a hand-held programmer 202 and/or a clinician programmer 204, assisted as required through the use of a directional device 206 (see FIG. 1). (The handheld programmer is thus considered to be in "telecommunicative" contact with the IPG; and the clinician programmer is likewise considered to be in telecommunicative contact with the IPG, e.g., through the hand-held programmer). The charging and forward telemetry circuitry 172 demodulates the carrier signal it receives through the coil 170 to recover the programming data, e.g., the operating program and/or the stimulation parameters, which programming data is then stored within the memory 162, or within other memory elements (not shown) distributed throughout the IPG 100.

The microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes E1 . . . En, and the like. Informational data sensed through the monitoring circuit 174 may be sent to a remote location external to the IPG (e.g., a non-implanted location) through back telemetry circuitry 176, including a transmission coil 177.

The operating power for the IPG 100 may be derived from a rechargeable power source 180 according to an exemplary embodiment of the present invention. The rechargeable power source 180 may comprise a lithium-ion or lithium-ion polymer battery, for example. The rechargeable battery 180 provides an unregulated voltage to power circuits 182. The power circuits 182, in turn, generate the various voltages 184, some of which are regulated and some of which are not, as needed by the various circuits located within the IPG 100.

In one exemplary embodiment, any of the n electrodes (En) may be assigned to up to k possible groups (where k is an integer corresponding to the number of channels). In one preferred embodiment, k may be equal to 4. Moreover, any of the n electrodes can operate, or be included in, any of the k channels. The channel identifies which electrodes are selected to synchronously source or sink current to create an electric field. Amplitudes and polarities of electrodes on a channel may vary, e.g., as controlled by the patient hand held programmer 202. External programming software in the clinician programmer 204 is typically used to set parameters including electrode polarity, amplitude, pulse rate and pulse width for the electrodes of a given channel, among other possible programmable features.

Hence, it is seen that each of the n programmable electrode contacts can be programmed to have a positive (sourcing current), negative (sinking current), or off (no current) polarity in any of the k channels. Moreover, it is seen that each of the n electrode contacts can operate in a bipolar mode or multipolar mode, e.g., where two or more electrode contacts are grouped to source/sink current at the same time. Alternatively, each of the n electrode contacts can operate in a monopolar mode where, e.g., the electrode contacts associated with a channel are configured as cathodes (negative), and the case electrode, on the IPG case, is configured as an anode (positive).

Further, according to an exemplary embodiment, the amplitude of the current pulse being sourced or sunk from a given electrode contact may be programmed to one of several discrete current levels. For example, the current pulse may be programmed to one of several discrete current levels between 0 to 10 mA, in steps of 0.1 mA. Also, in the exemplary embodiment, the pulse width of the current pulses is adjustable in convenient increments. For example, the pulse width range may be 0 to 1 milliseconds (ms) in increments of 10 microseconds (μs). Similarly, in the preferred embodiment, the pulse rate is adjustable within acceptable limits. For example, the pulse rate preferably spans 0-1000 Hz. Other programmable features can include slow start/end ramping, burst stimulation cycling (on for X time, off for Y time), and open or closed loop sensing modes.

The stimulation pulses generated by the IPG 100 may be charged balanced. This means that the amount of positive charge associated with a given stimulus pulse are offset with an equal and opposite negative charge. Charge balance may be achieved through a coupling capacitor, which provides a passive capacitor discharge that achieves the desired charge balanced condition. Alternatively, active biphasic or multi-phasic pulses with positive and negative phases that are balanced may be used to achieve the needed charge balanced condition.

Advantageously, the IPG 100 is able to individually control the n electrode contacts associated with the n electrode nodes E1, E2, E3, . . . En. Controlling the current sources 186 and switching matrix 188 using the microcontroller 160, in combination with the control logic 166 and timer logic 168, thereby allows each electrode contact to be paired or grouped with other electrode contacts, including the monopolar case electrode, to control the polarity, amplitude, rate, pulse width and channel through which the current stimulus pulses are provided. Other output circuits can be used with the invention, including voltage regulated output, multiplexed channels, and the like.

As shown in FIG. 3, much of circuitry included within the IPG 100 may be realized on a single application specific integrated circuit (ASIC) 190. This allows the overall size of the IPG 100 to be quite small, and readily housed within a suitable hermetically-sealed case. The IPG 100 may include n feedthroughs to allow electrical contact to be individually made from inside of the hermetically-sealed case with the n electrodes that form part of the lead system outside of the case.

As noted earlier, in use, the IPG 100 may be placed in a surgically-made pocket, e.g., in the abdomen or just at the top of the buttocks, and detachably connected to the lead system (comprising optional lead extension 120 and electrode array 110). While the lead system is intended to be permanent, the IPG 100 may be replaced should its power source fail, or for other reasons.

The back telemetry features of the IPG 100 allow the status of the IPG to be checked. For example, when the external hand-held programmer 202 (and/or the clinician programmer 204), initiates a programming session with the implant system 10 (FIG. 1), the capacity of the battery is telemetered so that the external programmer can calculate the estimated time to recharge. Any changes made to the current stimulus parameters are confirmed through back telemetry, thereby assuring that such changes have been correctly received and implemented within the implant system. Moreover, upon interrogation by the external programmer, all programmable settings stored within the implant system 10 may be uploaded to one or more external programmers.

Figure 4:
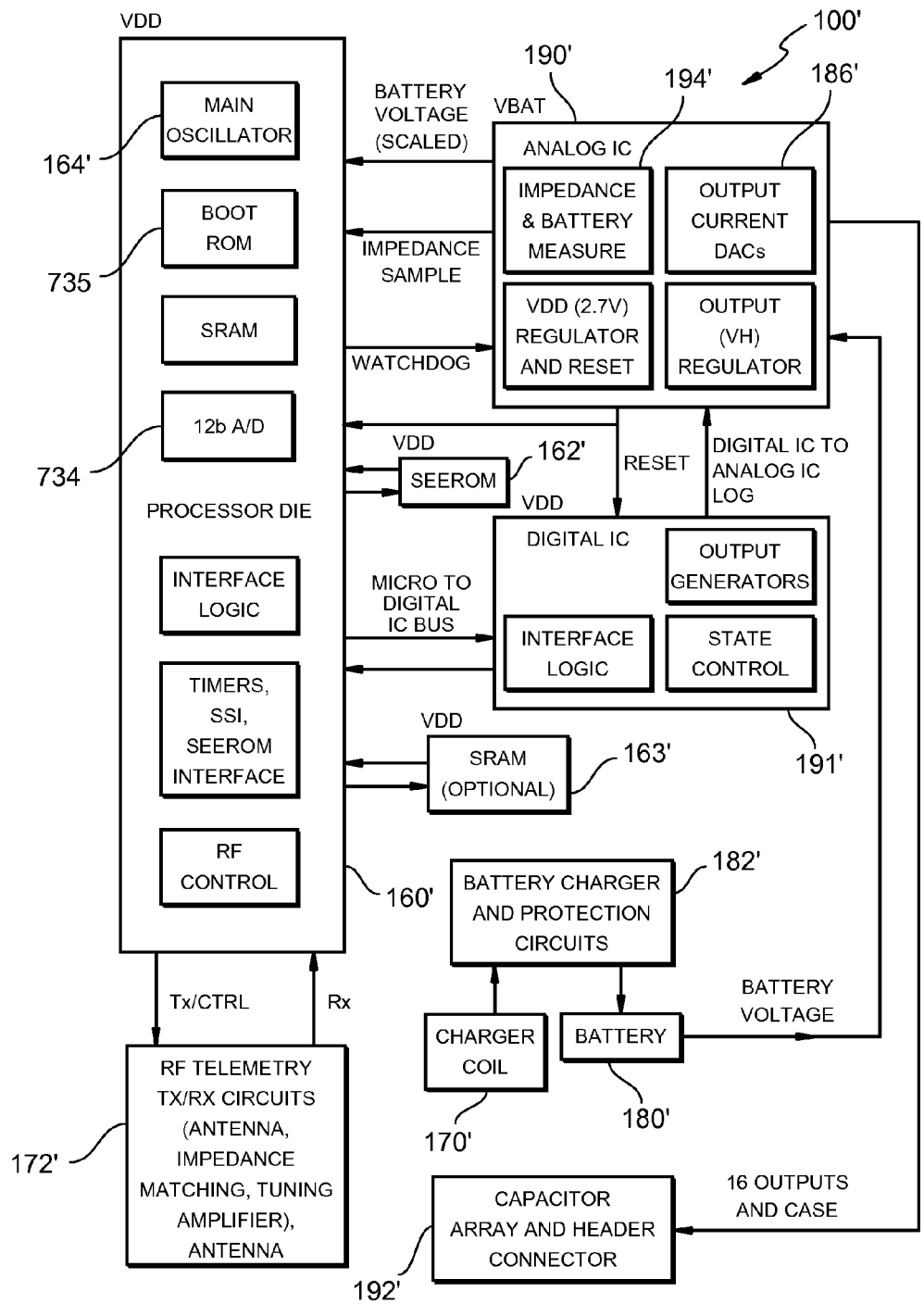
FIG. 4 shows a block diagram that illustrates another embodiment of an implantable pulse generator (IPG) that may be used with the invention.

Turning next to FIG. 4, a hybrid block diagram of an alternative embodiment of an IPG 100' that may be used with the invention is illustrated. The IPG 100' includes both analog and digital dies, or integrated circuits (ICs), which may be housed in a single hermetically-sealed rounded case having, for instance, a diameter of about 45 mm and a maximum thickness of about 10 mm. Many of the circuits contained within the IPG 100' are identical or similar to the circuits contained within the IPG 100, shown in FIG. 3. The IPG 100' includes a processor die, or chip, 160', an RF telemetry circuit 172' (typically realized with discrete components), a charger coil 170', a lithium ion or lithium ion polymer battery 180', battery charger and protection circuits 182', memory circuits 162' (SEEPROM) and 163' (SRAM), a digital IC 191', an analog IC 190', and a capacitor array and header connector 192'.

The capacitor array and header connector 192' include sixteen output decoupling capacitors, as well as respective feed-through connectors for connecting one side of each decoupling capacitor through the hermetically-sealed case to a connector to which the electrode array 110, or lead extension 120, may be detachably connected.

The processor 160' may be realized with an application specific integrated circuit (ASIC), field programmable gate array (FPGA), or the like that comprises a main device for full bi-directional communication and programming. The processor 160' may utilize an 8086 core (the 8086 is a commercially-available microprocessor available from, e.g., Intel), or a low power equivalent thereof, 16 kilobytes of SRAM memory, two synchronous serial interface circuits, a serial EEPROM interface, and a ROM boot loader 735. The processor die 160' may further include an efficient clock oscillator circuit 164' and a mixer and modulator/demodulator circuit implementing the QFAST RF telemetry method supporting bi-directional telemetry at 8 Kbits/second. QFAST stands for "Quadrature Fast Acquisition Spread Spectrum Technique," and represents a known and viable approach for modulating and demodulating data. An analog-to-digital converter (A/D) circuit 734 is also resident on the processor 160' to allow monitoring of various system level analog signals, impedances, regulator status and battery voltage. The processor 160' further includes the necessary communication links to other individual ASICs utilized within the IPG 100'. The processor 160', like all similar processors, operates in accordance with a program that is stored within its memory circuits.

The analog IC (AIC) 190' may comprise an ASIC that functions as the main integrated circuit that performs several tasks necessary for the functionality of the IPG 100', including providing power regulation, stimulus output, and impedance measurement and monitoring. Electronic circuitry 194' performs the impedance measurement and monitoring function.

The analog IC 190' may also include a number of output current sources 186'. The output current sources 186' are configured to supply current to a load, such as tissue, for example. The output current sources 186' may be configured to deliver up to 20 mA aggregate and up to 12.7 mA on a single channel in 0.1 mA steps. However, it will be noted that the output current sources 186' may be configured to deliver any amount of aggregate current and any amount of current on a single channel, according to one exemplary embodiment. The output current sources 186' will be described in more detail below.

Regulators for the IPG 100' supply the processor and the digital sequencer with a voltage. Digital interface circuits residing on the analog IC 190' are similarly supplied with a voltage. A programmable regulator supplies the operating voltage for the output current sources 186', e.g., sixteen bi-directional output current sources, each of which may be configured to either source or sink current as previously mentioned. Each output current source 186' may be connected to an electrode node (En; FIG. 3). Each electrode node, in turn, may be connected to a coupling capacitor Cn (FIG. 3). The coupling capacitors Cn and electrode nodes, as well as the remaining circuitry on the analog IC 186', may all be housed within the hermetically sealed case of the IPG 100. A feedthrough pin, which is included as part of the header connector 192', allows electrical connection to be made between each of the coupling capacitors Cn and the respective electrodes E1, E2, E3, . . . , or E16, to which each output current source 186' is associated.

The digital IC (DigIC) 191' functions as the primary interface between the processor 160' and the AIC output circuits 186'. The main function of the DigIC 191' is to provide stimulus information to the output current sources 186'. The DigIC 191' thus controls and changes the stimulus levels and sequences when prompted by the processor 160'. In an exemplary embodiment, the DigIC 191' comprises a digital application specific integrated circuit (digital ASIC).

Figure 5:
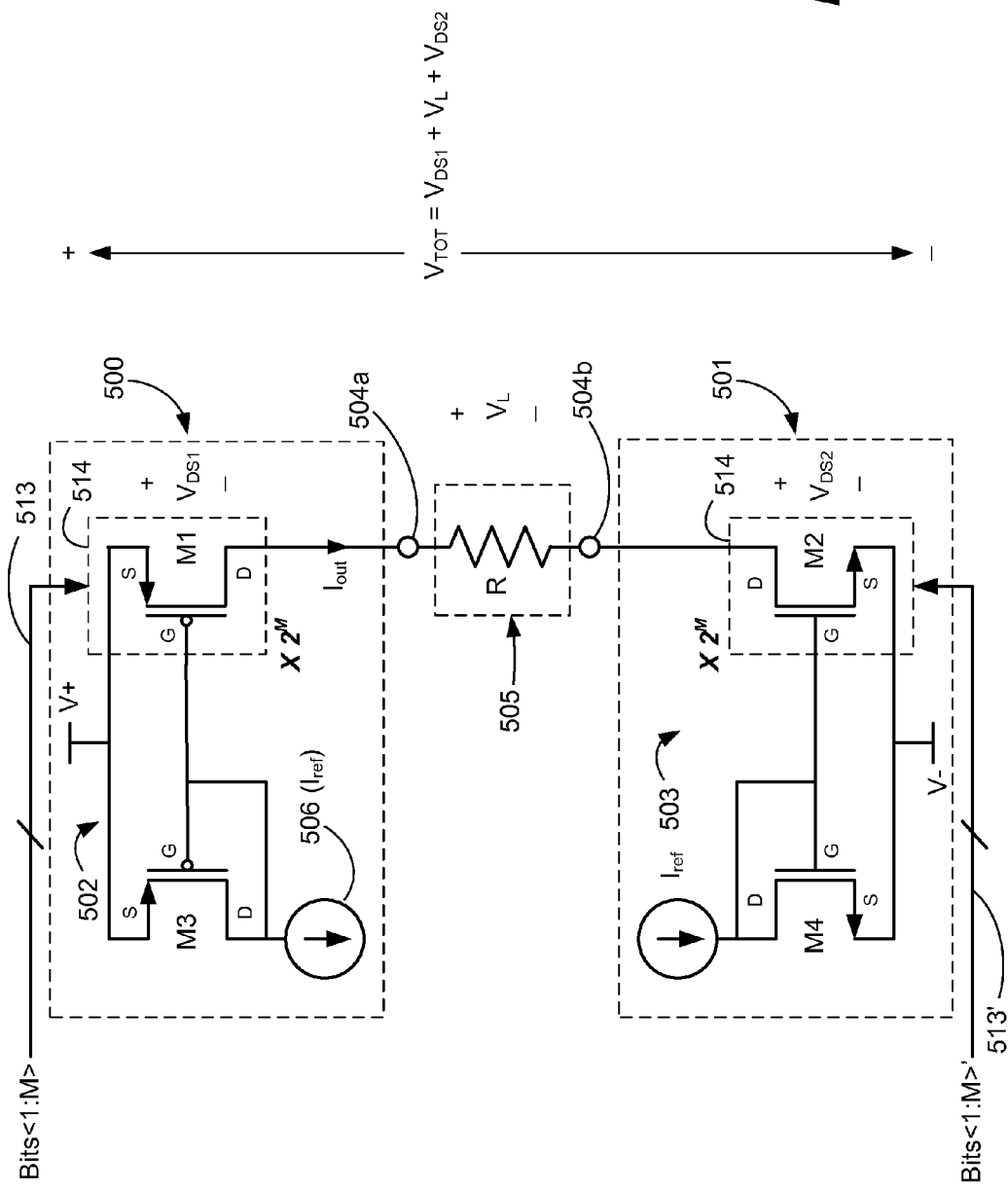
FIG. 5 shows an exemplary output current source and a corresponding output current sink each having current digital-to-analog converter (DAC) circuitry in series with a load.

In one exemplary embodiment of the present invention, each of the output current sources 186' of FIG. 4 may include a current digital to analog converter (DAC) configured to regulate the current that is delivered to the load. As mentioned previously, the current DAC is located in series with the load. FIG. 5 illustrates an exemplary output current source 500 and a corresponding output current sink 501 each having current DAC circuitry 502, 503 in series with load 505. The load 505 may be tissue or any other resistive load to which current is supplied.

As shown in FIG. 5, the output current source 500 may include a current generator 506 configured to generate a reference current, $I_{ref}$. A suitable current generator is disclosed in U.S. Pat. No. 6,181,969 ('969 patent), issued Jan. 30, 2001 in the name of inventor John C. Gord, which is incorporated herein by reference in its entirety. The current $I_{ref}$ is input into DAC circuitry 502, 503 which is configured to regulate and/or amplify $I_{ref}$ and to output an output current $I_{out}$. The relation between $I_{out}$ and $I_{ref}$ is determined in accordance with input bits arriving on bus 513, which gives DAC circuitry 502 its digital-to-analog functionality. Essentially, in accordance with the values of the various M bits on bus 513, any number of output stages 514 (i.e., M1) are tied together in parallel such that $I_{out}$ can range from $I_{ref}$ to $2^{M}*I_{ref}$. (Fractional values of $I_{ref}$ are also possible, as disclosed in the '969 patent, but such subtlety is ignored herein for simplicity). Although not shown in FIG. 5, the output stages 514 can contain other components, such as choke transistors and other transistors designed to ensure good current matching in the current mirror circuitry. However, as such structures are explained in the above-incorporated '969 patent, they are not discussed further, and the simpler view of DAC circuitry of FIG. 5 is used as a basis for discussion.

As noted above, the circuit of FIG. 5 also comprises an output current sink 501 corresponding to the output current source 500. The output current sink 501 in FIG. 5 preferably includes DAC circuitry 503, which is essentially similar in design to the DAC circuitry 502 of the output current source 500, although preferably formed of N-type MOS transistors M2, M4.

The output current source 500 is coupled to an electrode 504a, while the output current sink 501 is coupled to a different electrode 504b. As explained in the above-incorporated '969 patent, an electrode will typically be hard-wired to both an output current source 500 and an output current sink 501, only one (or neither) of which is activated at a particular time to allow the electrode to selectively be used as either a source or sink (or as neither). The source and sink hard-wired at each electrode are sometimes respectively referred to as PDACs and NDACs, reflecting the fact that the sources are typically formed of P-type transistors while the sinks are typically formed of N-type transistors. (The use of transistors of these polarities is sensible given that the source is biased to a high voltage (V+) on the analog IC 190', where P-type transistors are most logical, while the sink is biased to a low voltage (V−), where N-type transistors are most logical. The substrate connection (not shown) for the transistors would typically be tied to the appropriate power supply, either V+ or V−, but could also be tied to the source). Thus, as shown in FIG. 5, output current source 500 may be associated with electrode 5 (i.e., 504a) at a particular point in time, while output current sink 501 may be associated with electrode 7 (i.e., 504b) at that time. At a later time, electrodes 5 and 7 could be switched such that 5 now operates as the sink, while 7 operates as the source.

The M1/M3 and M2/M4 current mirrors require that transistors M1 and M2 operate in a saturation mode, such that the channels of the transistors are in "pinch off" When in a saturation mode, the output current $I_{out}$ is proportional to the gate voltage of the transistors M1 or M2, but does not depend upon the drain voltage to the first order. However, to keep the transistors M1 and M2 in the saturation mode, a certain drain-to-source voltage, $V_{DS}$, has to be satisfied for each transistor. Specifically, $V_{DS}$ must be greater than the gate-to-source voltage ($V_{GS}$) minus the threshold voltage ($V_T$) of the transistor (i.e., $V_{DS} > V_{GS} - V_T$). (This saturation condition is necessarily satisfied because $V_{DS} = V_{GS}$ by virtue of the common gate/drain connection of transistors M3 and M4). The minimum drain-to-source voltage $V_{DS}$ that satisfies this relationship and allows transistors M1 and M2 to operate in the saturation mode is typically 0.5 to 0.7 volts.

Assuming the load 505 has a resistance of R, the voltage drop across the load 505, $V_L$, is equal to $I_{out}*R$. Because the transistors M1 and M2 are in series with the load 505, the total voltage drop, $V_{TOT}$, due to the output current source 500, the output current sink 501, and the load 505 may represented by the following equation: $(V+)-(V-)=V_{TOT}=V_{DS1}+V_L+V_{DS2}$. The total power, $P_{TOT}$, consumed by the circuitry shown in FIG. 5 is equal to $V_{TOT}*I_{out}$. (It will be recognized by one skilled in the art that additional power may be consumed by transistors M3 and M4 and other circuitry that may be included in the output current source 500 and sink 501. However, for purposes of explaining the present invention, the power consumed by the circuitry shown in FIG. 5 will be represented by the equation $P_{TOT}=V_{TOT}*I_{out}$). In other words, the total power consumed by the DACs 502, 503 (and ultimately by the IPG 100) is in part determined by the voltage drops $V_{DSx}$ that occur across transistors M1 and M2, which as just noted are significant. Accordingly, the life of the battery or other power source for the IPG 100 is adversely affected by these voltage drops. Hence, a current DAC design that results in a reduction in the drain-to-source voltage drops $V_{DS1}$ and $V_{DS2}$ of M1 and M2 is highly desirable to reduce power consumption and prolong battery life.

Figure 6:
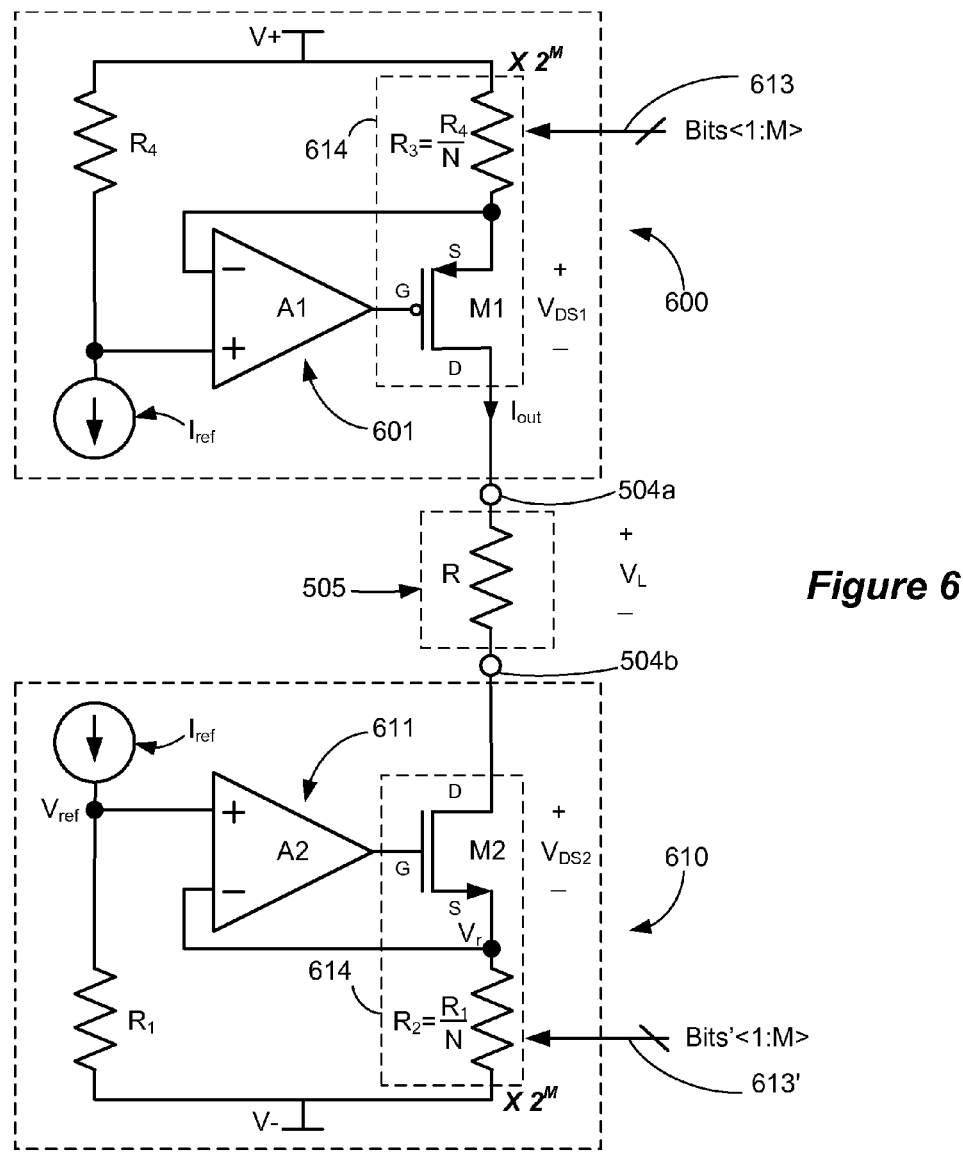
FIG. 6 shows a modified design for the output current source and sink of FIG. 5 in accordance with an embodiment of the present invention.

FIG. 6 illustrates an embodiment of the present invention in which an output current source 600 and its corresponding output current sink 610 respectively comprise DAC circuitry 601, 611 configured to regulate $I_{ref}$ and deliver a regulated and/or amplified current $I_{out}$ to load R. The DAC circuitry 601, 611 includes MOS transistors M1, M2 that do not have to operate in a saturation mode to provide the regulated output current $I_{out}$. According to one exemplary embodiment, the output current source/sink 600, 610 may be used as the output current source/sink 186' in the IPG 100' of FIG. 4.

While both the output current source and sink 600, 610 are shown in FIG. 6, it should be understood that the invention can comprise either of these circuits separately. Moreover, output current source 600 could be used with a different output current sink than that shown as 610, or could be used with no corresponding output current sink. Likewise, output current sink 610 could be used with a different output current source than that shown as 600, or could be used with no corresponding output current source. However, because it is preferred to use both a source and sink together in an IPG application, and because it is preferred for convenience that the designs be symmetrical for each, the source and sink are so depicted in FIG. 6.

As shown in FIG. 6, the DAC circuitry 601, 611 in one embodiment is similar in design, and preferably comprises P-type MOS transistors in the output current source 600 and N-type MOS transistors in the output current sink 610. However, this is not strictly required, and devices of different polarities could be used in either the source 600 or sink 610 with the same advantages. As with the output current source/sink 500/510 of FIG. 5, the output stages 614 can be multiplied in conjunction with the status of the digital bits on bus 613 such that $I_{out}$ can range from $I_{ref}$ to $2^{M}*I_{ref}$. However, because the analog aspects of the DAC circuitry are most important to illustration of embodiments of the invention, such analog aspects are the focus of the circuitry depicted in FIG. 6. The digital aspects of the DAC circuitry are discussed in further detail in the above-incorporated '969 patent.

DAC circuitry 601 or 611 in the embodiment of FIG. 6 comprises a MOS transistor (M1 or M2), an operational amplifier (op amp) (A1 and A2), and two resistors ($R_1$ and $R_2$, or $R_3$ and $R_4$). Because believed easiest to explain, the operation of the output current sink 610 is described below. It should be understood that the output current source 600 would operate using similar principles, although modified to account for changes in the polarity of the circuits used compared to the sink 610. Moreover, while the use of an N-type MOS transistor M2 is shown for use in the output current sink 610, it is again worth mentioning that devices of different polarities can be used in other useful embodiments.

As shown in FIG. 6, a pair of resistors $R_1$ and $R_2$ matched with a resistive ratio N are coupled together through a negative feedback network. Because the operational amplifier A2 has a very high impedance, $V_{REF}$ (i.e., $I_{ref}*R_1$) is propagated to $V_r$ by the feedback network: should $V_r$ fall below $V_{REF}$, then the output of op amp A2 would be increased, which would tend to turn transistor M2 further on. This increases $I_{out}$, which in turn increases $V_r$ (i.e., $I_{out}*R_2$), at least until such time as $V_r$ would exceed $V_{REF}$ at which point the feedback loop would have the opposite effect. Because in a steady state $V_{REF}=V_r$, it can be seen that the ratio N between $R_1$ and $R_2$ defines the current gain of the DAC circuitry 610 (i.e., $I_{out}=N*I_{ref}$).

Importantly, transistor M2 does not have to operate in saturation mode to provide the regulated output current, $I_{out}$. Thus, the drain-to-source voltage drop $V_{DS2}$ of M2 may be significantly lower than the drain-to-source voltage drop $V_{DS2}$ of M2 in FIG. 5—less than 0.2 volts, for example. The same is true for transistor M1 in the current output source 600, which will experience a drop $V_{DS2}$ of less than 0.2 volts, again less than corresponding transistor M1 in FIG. 5. While resistors R3 and R2 are also in the output stage, and therefore will result in voltage drops that consume some power, such voltage drops will normally be minimal because these resistances will generally by at least an order of magnitude smaller than the "on" resistances of the transistors M1 and M2 and the load R. For example, R3 and R2 may be ohms or tens of ohms, which would be negligible compared to the "on" resistances of transistors M1 and M2, as well as load R (typically on the order of hundreds or thousands of ohms). Thus, the DAC circuitry topology of FIG. 6 advantageously reduces the amount of power that is consumed by the output current source 600. It is important to note that, according to a preferred embodiment, the drain-to-source voltage drop $V_{DS}$ may be any voltage that is less than the drain-to-source voltage drop required for transistors M1, M2 to operate in saturation mode.

An additional advantage of the current DAC circuitry topology of FIG. 6 is that the amplification of the input current $I_{ref}$ may be easily adjusted by adjusting the values of $R_1$ and $R_2$ (and $R_3$ and $R_4$), which are related by the ratio, N. As mentioned previously, the output current, $I_{out}$, is equal to N times the input current, $I_{ref}$. Therefore, the current gain may be increased merely by changing the ratio N between $R_1$ and $R_2$ (and $R_3$ and $R_4$). In contrast, multiple stages 514 of transistors must be added to the current DAC topology of FIG. 5 to amplify the input current, $I_{ref}$. For example, FIGS. 7A and 7B respectively show the output current sources 500 and 600 of FIGS. 5 and 6 for exemplary output currents, $I_{out}$, of $I_{ref}$, $2I_{ref}$, and $4I_{ref}$. In the design of FIG. 5 (FIG. 7A), increasing the current requires multiplying in parallel the number of devices (i.e., transistors) in output stages 514 by a factor of $2^M$. In other words, at least $2^M$ devices (potentially hundreds or thousands) must be fabricated on the analog IC 190'. (See FIGS. 8A and 8B of the above-incorporated '969 patent and associated text for further details). By contrast, when the design of FIG. 6 is used (FIG. 7B), the number of devices in the output stages 614 does not change as higher output currents are called for; instead, only the values of the resistors ($R_1$ and $R_2$; $R_3$ and $R_4$) change. Thus, the preferred current DAC circuitry topology of FIG. 6 simplifies overall IPG 100 design and reduces layout requirements.

Figure 8:
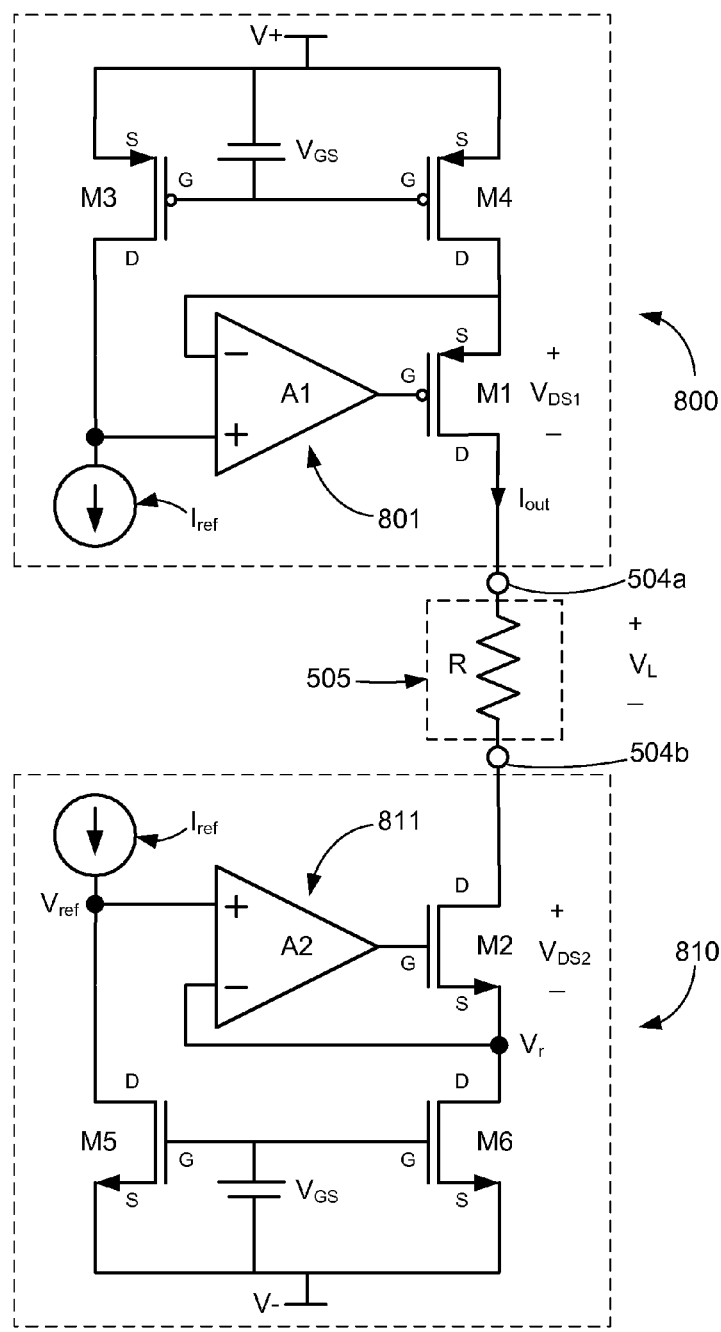
FIG. 8 shows another modified design for the output current source and sink of FIG. 5 in accordance with an embodiment of the present invention.

FIG. 8 illustrates a preferred alternative embodiment of the present invention in which an output current source 800 and an output current sink 810 comprise an alternative DAC circuitry topology 801, 811 configured to regulate $I_{ref}$ and deliver a regulated and/or amplified current $I_{out}$ to a load, R. As with the embodiment of FIG. 6, an embodiment of the invention can comprise either circuit 800 or 810 individually, although in an IPG application it is preferred to use two similarly-designed sources/sinks together. Moreover, the polarities of the devices used in both the output current source 800 and output current sink 810 can be changed from what is depicted. Because believed easiest to explain, the operation of the output current sink 810 is described below, although it should be understood that the symmetric output current source 800 would operate using similar principles, although modified to account for changes in the polarity of the devices used.

As will be explained in detail below, the DAC circuitry 811 of the output current sink 810 preferably includes N-type MOS transistors M2, M5, and M6 that, like the embodiment of FIG. 6, do not have to operate in saturation mode to provide the regulated output current $I_{out}$. MOS transistors M5 and M6 form matched active loads. Op Amp A2 and transistor M2 are configured to act as a feedback loop to control the drain voltage of M2, resulting in $V_r=V_{REF}$. In a preferred embodiment, the common gate of M5 and M6 are biased (via $V_{GS}$) such that M5 and M6 operate in a linear mode as opposed to a saturation mode, and hence have small voltage drops from source to drain. Hence, the totality of the drain-to-source drops (i.e., across M2 and M6) may be significantly lower than the drain-to-source voltage drop $V_{DS1}$ of M2 in FIG. 5—less than 0.2 volts, for example. The same is true for transistors M1, M4 in the output current source 800, which are likewise not in saturation. Thus, the preferred current DAC circuitry topology 801, 811 of FIG. 8 advantageously reduces the amount of power that is consumed by the output current source 800 and/or the output current sink 810.

In one embodiment, transistors M5 and M6 (and M3 and M4) are identical, and hence have identical drain-to-source resistances. However, in other useful embodiments, these drain-to-source resistances can be modified to achieve the benefits of FIG. 6, such as increased output current gains using simplified layouts, as discussed earlier. For example, assume that transistor M5 is N times more resistive than transistor M6, for example, by increasing M5's channel length by N or decreasing M5's channel width by N. The two transistors M5, M6 of FIG. 8 would then stand in the same relationship as do resistors $R_1$ and $R_2$ of FIG. 6, thus allowing the circuit to provide an output current gain that is N times larger than the reference current ($I_{out}=N*I_{ref}$).

As with the embodiment of FIG. 6, the embodiment of FIG. 8 may be extended to operate as a multi-bit DAC, although such structures (like bit bus 613, stages 614, etc.) are not shown in FIG. 8 for convenience.

Figure 9:
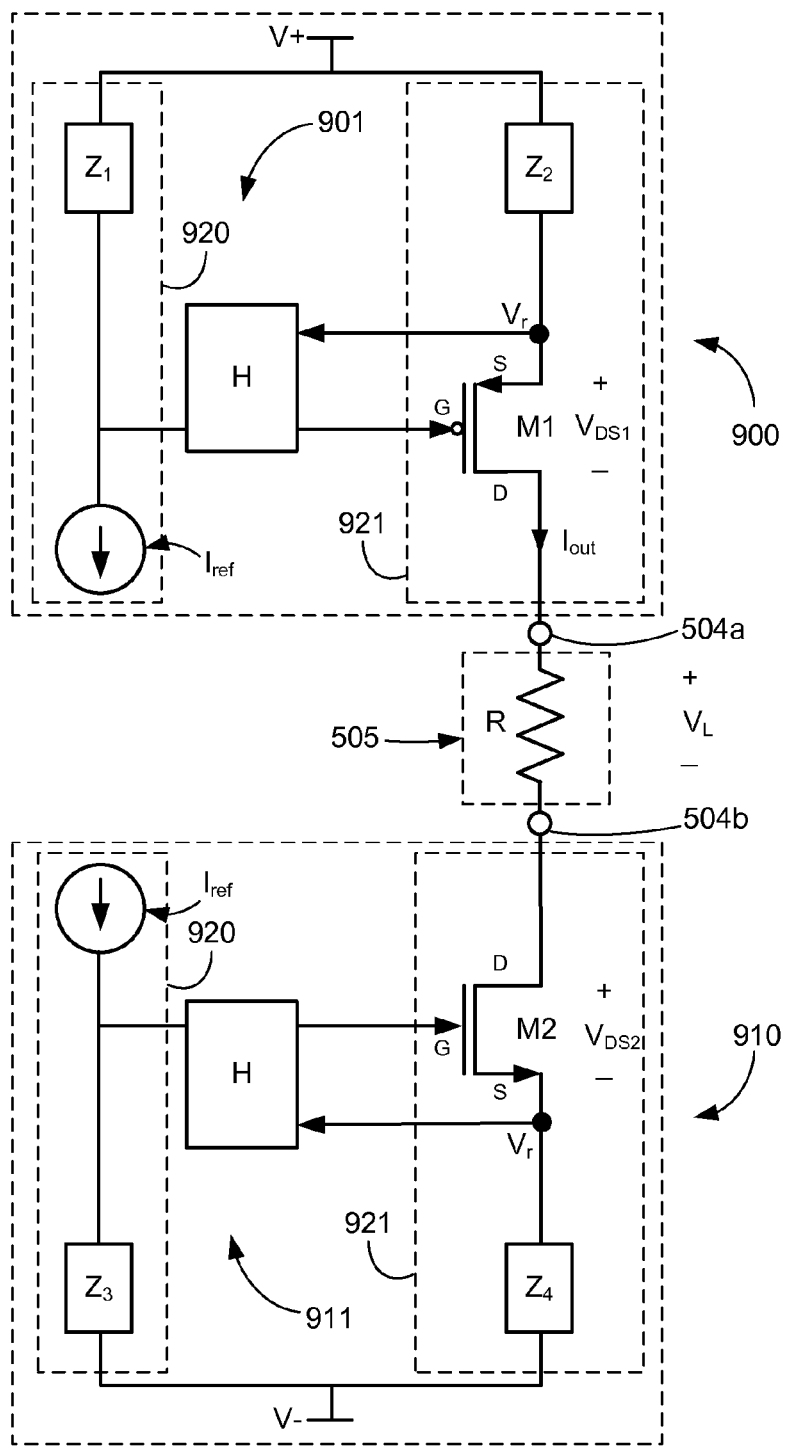
FIG. 9 shows the design of the improved output current source or sink illustrated generically with loads and a feedback circuit.

The approaches of FIGS. 6 and 8 are generically illustrated in FIG. 9, which shows a generic structure for an output current source 900 and an output current sink 910. The DAC circuitry 901, 911 for each comprises two loads ($Z_1$ and $Z_2$; $Z_3$ and $Z_4$), and a feedback circuit, H for controlling the gate of the transistor M1 or M2 so as to operate that transistor in a linear mode, but not a saturation mode. In fact, the circuits can even be further generalized when it is realized that the loads $Z_x$ can comprise part of the feedback circuit H. What is important is to receive feedback concerning the mode in which the transistors M1 or M2 are operating so that these transistors can be controlled to operate in a linear mode, which is most easily accomplished by monitoring the voltages at nodes on the input path 920 and the output path 921. As several such circuits are possible of achieving this result, it should be understood that the circuits of FIGS. 6 and 8 are merely exemplary.

It should be understood that the direction in which current flows is a relative concept, and different conventions can be used to define whether currents flow to or from various sources. In this regard, arrows showing the directions of current flows in the Figures, references to current flowing to or form various circuit nodes, references to currents being sunk or sourced, etc., should all be understood as relatively and not in any limiting sense.

It should also be understood that reference to an "electrode" implantable adjacent to a tissue to be stimulated includes electrodes on the implantable stimulator device, or associated electrode leads, or any other structure for stimulating tissue.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. An implantable stimulator device, comprising:
    a first electrode implantable adjacent to tissue to be stimulated;
    at least one first transistor configured to source a stimulation current along a first output path to the first electrode;
    a second electrode implantable adjacent to tissue to be stimulated; and
    at least one second transistor configured to sink the stimulation current along a second output path from the second electrode,
    wherein the at least one first transistor and the at least one second transistor are controlled to operate in a linear mode.

2. The device of claim 1, wherein the at least one first transistor and the at least one second transistor are controlled using feedback from the first and second output paths respectively.

3. The device of claim 1, further comprising a first feedback circuit for controlling the at least one first transistor by receiving a first voltage from the first output path, and a second feedback circuit for controlling the at least one second transistor by receiving a second voltage from the second output path.

4. The device of claim 3, wherein the first and second feedback circuits respectively also receive first and second reference voltages, and wherein the first and second feedback circuits respectively control the at least one first transistor and the at least one second transistor by comparing the first and second voltages to the first and second reference voltages.

5. The device of claim 4, wherein the first and second reference voltages are respectively generated using first and second constant current sources.

6. The device of claim 3, wherein the first and second feedback circuits respectively comprise first and second amplifiers.

7. The device of claim 1, further comprising a first resistance in the first output path between the at least one first transistor and a first power supply voltage, and a second resistance in the second output path between the at least one second transistor and a second power supply.

8. The device of claim 7, further comprising a first feedback circuit for controlling the at least one first transistor by receiving a first voltage between the first resistance and the at least one first transistor, and a second feedback circuit for controlling the at least one second transistor by receiving a second voltage between the second resistance and the at least one second transistor.

9. The device of claim 8, wherein the first and second feedback circuits respectively also receive first and second reference voltages, and wherein the first and second feedback circuits respectively control the at least one first transistor and the at least one second transistor by comparing the first and second voltages to the first and second reference voltages.

10. The device of claim 9, wherein the first and second feedback circuits respectively comprise first and second amplifiers.

11. The device of claim 9, wherein the first and second reference voltages are respectively generated by passing first and second currents through third and fourth resistances.

12. The device of claim 11, wherein the stimulation current is N times higher than the first and second currents.

13. The device of claim 12, wherein N is proportional to the ratio of the first and third resistances, and the ratio of the second and fourth resistances.

14. An implantable stimulator device, comprising:
    a first electrode implantable adjacent to tissue to be stimulated;
    a first load configured to source a current along a first output path to the first electrode;
    a first feedback circuit configured to receive a first voltage on the first output path, and to control the first load to source the current along the first output path;
    a second electrode implantable adjacent to tissue to be stimulated;
    a second load configured to sink the current along a second output path from the second electrode; and
    a second feedback circuit configured to receive a second voltage on the second output path, and to control the second load to sink the current along the second output path.

15. The device of claim 14, wherein the first and second loads comprise transistors.

16. The device of claim 15, wherein the first and second feedback circuits respectively control the transistors to operate in a linear mode.

17. The device of claim 14, wherein the first and second feedback circuits respectively also receive first and second reference voltages, and wherein the first and second feedback circuits respectively control the first and second load by comparing the first and second voltages to the first and second reference voltages.

18. The device of claim 17, wherein the first and second reference voltages are respectively generated using first and second constant current sources.

19. The device of claim 14, wherein the first and second feedback circuits respectively comprise first and second amplifiers.

20. The device of claim 14, further comprising a third load in the first output path between the first load and a first power supply voltage, and a fourth load in the second output path between the second load and a second power supply.

21. The device of claim 20, wherein the first voltage is between the first and third loads, and wherein the second voltage is between the second and fourth loads.

22. The device of claim 21, wherein the first and second feedback circuits respectively also receive first and second reference voltages, and wherein the first and second feedback circuits respectively control the first and second loads by comparing the first and second voltages to the first and second reference voltages.

23. The device of claim 22, wherein the first and second feedback circuits respectively comprise first and second amplifiers.

24. The device of claim 22, wherein the first and second reference voltages are respectively generated by passing first and second currents through fifth and sixth loads.

25. The device of claim 24, wherein the stimulation current is N times higher than the first and second currents.

26. The device of claim 25, wherein N is proportional to the ratio of resistances of the third and fifth loads, and the ratio of resistances of the fourth and sixth loads.

* * * * *